(12) United States Patent
Farber

(10) Patent No.: US 12,357,587 B2
(45) Date of Patent: *Jul. 15, 2025

(54) CANNABINOID MONOTERPENE BASED PHARMACEUTICAL TOPICAL COMPOSITION FOR MUSCULOSKELETAL PAIN

(71) Applicant: MOUNTAIN VALLEY MD INC., Vaughan (CA)

(72) Inventor: Michael Farber, Livingston, NJ (US)

(73) Assignee: MOUNTAIN VALLEY MD INC., Vaughan (CA)

( * ) Notice: Subject to any disclaimer, the term of this patent is extended or adjusted under 35 U.S.C. 154(b) by 498 days.

This patent is subject to a terminal disclaimer.

(21) Appl. No.: 17/844,139

(22) Filed: Jun. 20, 2022

(65) Prior Publication Data

US 2023/0255899 A1   Aug. 17, 2023

Related U.S. Application Data

(63) Continuation-in-part of application No. 17/671,852, filed on Feb. 15, 2022, now Pat. No. 11,395,813.

(51) Int. Cl.
| | | |
|---|---|---|
| A61K 36/00 | (2006.01) | |
| A61K 9/00 | (2006.01) | |
| A61K 9/06 | (2006.01) | |
| A61K 31/015 | (2006.01) | |
| A61K 31/05 | (2006.01) | |
| A61K 36/81 | (2006.01) | |
| A61K 47/20 | (2006.01) | |
| A61K 47/22 | (2006.01) | |
| A61P 29/00 | (2006.01) | |

(52) U.S. Cl.
CPC ............ *A61K 31/05* (2013.01); *A61K 9/0014* (2013.01); *A61K 9/06* (2013.01); *A61K 31/015* (2013.01); *A61K 36/81* (2013.01); *A61K 47/20* (2013.01); *A61K 47/22* (2013.01); *A61P 29/00* (2018.01)

(58) Field of Classification Search
CPC ....................................................... A61K 47/20
See application file for complete search history.

(56) References Cited

U.S. PATENT DOCUMENTS

2018/0221333 A1* 8/2018 Dollard .................... A61P 15/00
2018/0339008 A1* 11/2018 Klele ...................... A61K 31/05

* cited by examiner

*Primary Examiner* — Qiuwen Mi
(74) *Attorney, Agent, or Firm* — Michael J. Feigin, Esq.; Feigin and Fridman LLC

(57) ABSTRACT

A topical pain relief composition has a base with a mixture of various components such as, but not limited to, a base, d-limonene, cannabinoids or a derivative thereof, ashwagandha extracts and dimethyl sulfoxide (DMSO).

12 Claims, No Drawings

CANNABINOID MONOTERPENE BASED PHARMACEUTICAL TOPICAL COMPOSITION FOR MUSCULOSKELETAL PAIN

FIELD OF THE INVENTION

The subject matter described herein generally relates to topical pharmaceutical compositions including cannabinoids and monoterpenes. More specifically, the present invention relates to topical pharmaceutical compositions including cannabinoids and monoterpenes for the treatment of muscle and joint pain.

BACKGROUND

Pain is one of the most common forms of medical problem that people face and is a common reason for which people seek medical care. Pain also results in a tremendous number of lost work days per year.

There are three general classes of pain: nociceptive pain, neuropathic pain and psychogenic pain. The different types of diseases which emerge from said classes of pain include allodynia and multiple sclerosis.

Nociceptive pain occurs when the stimulation of the sensory nerve endings called nociceptors causes the sensation of pain. The nociceptive pain is often experienced when a body tissue is damaged after a surgery or after an external injury such as a sports injury or a dental procedure. The pain signals are transmitted by the nociceptors to the brain. The nociceptive pain is often localized, constant and has an aching or throbbing quality. Once the damage to the body tissue heals, the nociceptive pain usually resolves. The nociceptive pain may be resolved through treatment with opioids.

Psychogenic pain is a pain disorder that is associated with psychological factors for example, mental, emotional or behavioral factors. The said factors can also increase or prolong the psychogenic pain. Headaches, muscle pains, back pain, and stomach pains are some of the most common types of psychogenic pain. The diagnosis is made when all physical causes of the psychogenic pain are ruled out.

Neuropathic pain is the result of an injury or malfunction of the peripheral or the central nervous system. The pain may be triggered by an injury but not necessarily by an injury of the nervous system itself. The pain is caused due to abnormalities in various levels of the nervous system such as, the peripheral nerves, the spinal cord and the brain. Neuropathic pain is frequently chronic and is often less responsive to treatment with opioids, but may respond to treatment with anticonvulsant or antidepressant drugs.

Neuropathic pain is a chronic type of nonmalignant pain with an estimated prevalence of over lot of the population. Optimizing the pain relief in patients suffering from neuropathic pain is crucial in helping the patient regain control of his or her life.

The neuropathic pain is most commonly caused due to an injury or dysfunction of the peripheral nerves or nerves descending from the spinal cord which results in disinhibition of nerve impulses at the spinal cord which in turn results in pain. Neuropathic pain can also be centrally mediated, rather than peripheral, in conditions such as spinal cord injury and multiple sclerosis.

Neuropathic pain can therefore be divided into two further classes; peripheral neuropathic pain and central neuropathic pain depending on whether the peripheral or central nervous system is affected.

Patients with peripheral neuropathic pain often experience pain which feels like a burning or electrical pain, whereas others describe their pain as feeling like extreme cold or pins and needles. The pain may be worsened by performing an activity or by wearing clothes over the affected area where the pain sensations are felt. The pain may also follow a daily pattern, which may mean the pain has worsened at certain times of the day.

Allodynia is a type of peripheral neuropathic pain. Allodynia is a painful response to a typically non-painful stimulus, for example, brushing the affected area with a fingertip. The allodynia pain tends to increase with repeated stimulation and may spread from the affected area. Allodynic pain can be evoked in response to chemical, thermal (cold or heat) or mechanical, low or high intensity stimuli applied either statically or dynamically to skin, joints, bone, muscle or viscera.

The patients suffering from neuropathic pain can have their quality of life greatly affected by it. The pain can interfere with work and social activities as well as with the amount and quality of sleep that a patient experiences. A successful treatment for the relief of neuropathic pain should improve both the amount of pain that the patient is experiencing as well as improving the patient's quality of life. Some non-pharmaceutical methods of treating the neuropathic pain include transcutaneous electrical nerve stimulation (TENS) and acupuncture.

However, the use of pharmaceuticals is the most common treatment for the neuropathic pain. The pharmaceuticals include topical creams applied directly to the site of pain or drug classes such as, analgesics, antidepressants and anticonvulsants are generally administered to treat the neuropathic pain. The drug carbamezepine, which is an anticonvulsant, is currently the only FDA approved drug which has an indication for neuropathic pain. It has been suggested in post marketing studies that there is a five- to eight-fold increase in the risk of blood dyscrasias in patients taking carbamezepine. In 7% of patients, a 25% decrease in their white blood cell count has been observed which is usually reversed within the first 4 months of therapy.

The use of cannabis as a medicine has long been known and during the 19th century and preparations of cannabis were recommended as a hypnotic sedative which were useful for the treatment of hysteria, delirium, epilepsy, nervous insomnia, migraine, pain and dysmenorrhea. Cannabinoids are a group of chemicals known to activate cannabinoid receptors in cells and are found in cannabis plants and are also produced endogenously in humans and other animals, these are termed endocannabinoids. Synthetic cannabinoids are chemicals with similar structures to plant cannabinoids or endocannabinoids.

Until recent times the administration of cannabis to a patient could only be achieved by preparing the cannabis by decoction which could then be swallowed, or by inhaling the vapours of cannabis by smoking the dried plant material. Recent methods have sought to find new ways to deliver cannabinoids to a patient including those which bypass the stomach and the associated first pass effect of the liver which can remove up to 90% of the active ingested dose and avoid the patient having to inhale unhealthy tars and associated carcinogens into their lungs.

Formulations containing specific, defined ratios of cannabinoids may be formulated from pure, synthetic cannabinoids or from extracts derived from the cannabis plant in combination with pharmaceutical carriers and excipients.

Some plant cannabinoids are purified to such an extent that all of the other naturally occurring compounds, such as, other minor cannabinoids and molecules such as terpenes are removed. This purification results in a purity of greater than 99% (w/w) of the target cannabinoid. To a certain extent, these purified cannabinoids can be considered to be the same as synthetic cannabinoids as they consist only of the target cannabinoid.

In one of the relevant prior arts, the cannabinoids-cannabidiol (CBD) was administered as a purified compound which partially relieved neuropathic pain. This was shown using the neuropathic pain model of chronic constriction injury of the rat sciatic nerve and testing the effectiveness of the test article with thermal and mechanical hyperalgesia and mechanical allodynia. These animal models were used to predict the effectiveness of a test compound on neuropathic pain.

Another relevant prior art, relates to a composition comprising of cannabinoids such as cannabidiol (CBD) and tetrahydrocannabinol (THC), wherein the ratio of CBD:THC by weight is between 18:1 and 30:1 for the treatment of neuropathic pain.

The cited prior arts present a composition which includes only cannabinoids. However, said compositions with the presence of only cannabinoids, partially relieve the pain in the affected area. Therefore, there is a need for a topical pharmaceutical composition which rapidly and effectively relieves the muscle and joint pain.

SUMMARY OF THE DISCLOSED TECHNOLOGY

In view of the deficiencies of the prior art compositions, the objective of the present invention is to provide a topical pharmaceutical composition which comprises of (including consisting essentially of or consisting of) a base, monoterpenes, cannabinoids, extracts of ashwagandha and dimethyl sulfoxide (DMSO).

Another objective of the present invention is to provide the topical pharmaceutical composition for relieving muscle pain and joint pain.

In an embodiment, the pharmaceutical composition may comprise cannabinoids in a range of 2% to 15% by weight of the pharmaceutical composition. In an embodiment, the pharmaceutical composition may comprise dimethyl sulfoxide in a range of 0.1% to 2% by weight of the pharmaceutical composition. In another embodiment, the amount of DMSO may be in a range of 1% to 2% by weight of the pharmaceutical composition. In an embodiment the monoterpene is d-limonene in an amount from 1% to 10% by weight of the composition. In an embodiment, the amount of base, d-limonene, cannabinoids, ashwagandha extracts and dimethyl sulfoxide (DMSO) present in the topical pharmaceutical composition may vary according to the requirements.

In an embodiment, the cannabinoids may be selected from a group consisting of cannabidiol (CBD) and tetrahydrocannabinol (THC). In an embodiment, the cannabinoids may be selected as only CBD and/or consists only of CBD. In an alternate embodiment, the cannabinoids may be selected as CBD in combination with THC. In an embodiment, the THC may be selected from a group consisting of delta 8 THC, delta 9 THC, and delta 10 THC. In an embodiment, the THC may be delta 8 THC which is a non-psychoactive compound. In an embodiment, the CBD may be a purified plant extract. In another embodiment, the CBD may be synthetic CBD. In an embodiment, the THC may be a purified plant extract. In another embodiment, the THC may be synthetic THC.

In an embodiment, the base may be selected from a group consisting of cream, gel or lotion. In an embodiment, the base may be a cream base and may comprise of vitamin-E.

In an embodiment, a method for preparing a topical pharmaceutical composition is disclosed. The method may comprise the steps of forming a first mixture, forming a second mixture, mixing and storing the first mixture and the second mixture to obtain a third mixture and filtering the third mixture to obtain a filtered third mixture and adding the filtered third mixture to a base.

In an embodiment, the first mixture may be formed by solubilizing CBD with an alcoholic-limonene based extract. In an embodiment, the first mixture may comprise CBD in a range of 50% to 80% by weight of first mixture. In an embodiment, the solubilizing of CBD with the alcoholic-limonene based extract may be performed in ratio of 1:1. In an embodiment, the alcoholic-limonene based extract may be ethanol-limonene based extract. In an embodiment, the ethanol-limonene based extract may include 40% to 60% of ethanol by weight of the ethanol-limonene extract.

In an embodiment, the solubilized CBD with the alcoholic-limonene based extract may be refrigerated (from 0 to 5 degrees Celsius) in absence of light for a period of 3 days, thereby forming a first mixture. In an embodiment, the second mixture may be formed by mixing the ashwaganda extracts and the dimethyl sulfoxide (DMSO) in water. In an embodiment, the second mixture may comprise dimethyl sulfoxide in an amount of 10% by weight of the second mixture. In an embodiment, the first mixture and the second mixture may be mixed, fitered, and stored in a desiccator for a predefined period and at a predefined temperature and to obtain a third mixture.

In an embodiment, the first mixture and the second mixture may be stored in the desiccator for a predefined period of 48 hours to 72 hours and at a predefined temperature of 35 degrees Celsius (or a range between 35 and 40 degrees). In an embodiment, the alcoholic content from the first mixture and the second mixture may be evaporated when the first mixture and the second mixture is stored in the desiccator. The above mixture is then, in embodiments of the disclosed technology, combined in a cream base or gel base resulting in the percentage mixture of d-limonene, cannabinoids, ashwaganda extract and DMSO described above. In some embodiments, emollients, penetration enhancers, and scents are added. Anti-inflammatory agents may further be added to the cream or gel, such as pharmaceutical or natural based anti-inflammatory molecules.

In an embodiment, the third mixture may be filtered to remove un-dissolved ashwagandha extracts and to obtain a filtered third mixture of dissolved ashwagandha extracts with cannabinoids, d-limonene and dimethyl sulfoxide (DMSO). In an embodiment, the filtered third mixture is added to a base, thereby obtaining the pharmaceutical composition of the present invention. In an embodiment, the pharmaceutical composition may act as a medicament for relieving muscle pain and joint pain. In an embodiment, the pharmaceutical composition may be applied to affected area where the sensation of pain is felt.

Any device or step to a method described in this disclosure can comprise, or consist of, that which it is a part of, or the parts which make up the device or step. The term "and/or" is inclusive of the items which it joins linguistically and each item by itself. Any element or described portion of the devices shown can be "substantially" as such, if used in the claims in this manner. Where used, "substantially" is defined as "within a 5% tolerance level thereof."

DETAILED DESCRIPTION OF EMBODIMENTS OF THE DISCLOSED TECHNOLOGY

As used herein, the term "topical pharmaceutical composition" refers to a composition comprising a base, d-limonene, cannabinoid, ashwagandha extracts and dimethyl sulfoxide (DMSO), wherein the composition is amenable to investigation for a specified, efficacious outcome in a mammal (for example, without limitation, a human).

The pharmaceutical composition described herein comprises of a mixture of various components such as, but not limited to, a base, d-limonene, cannabinoids or a derivative thereof, ashwagandha extracts and dimethyl sulfoxide (DMSO).

The component, cannabinoids or a derivative thereof as referred herein, is a chemical substance found in cannabis plant. Cannabinoids activate cannabinoid receptor cells in the body and brain of human beings. Cannabinoids act as a medicament for relieving pain including, but not limited to, muscle pain and joint pain, hysteria, delirium, epilepsy, nervous insomnia, migraine, and dysmenorrhea.

The cannabinoids are selected from a group consisting of cannabidiol (CBD) and its derivatives. The cannabinoids may be purified plant extracts or synthetic cannabinoids.

The CBD is present as a cannabis-based medicine extract (CBME). In one embodiment, the CBME may be produced by extraction with supercritical or subcritical $CO_2$. In an alternative embodiment, the CBME may be produced by extraction from a cannabis plant material by volatilization with a heated gas.

In an embodiment, the CBME may include all of naturally occurring cannabinoids in the cannabis plant material. In another embodiment, the CBME may be a purified naturally occurring cannabinoid. In an alternate embodiment, the CBME may be a synthetic cannabinoid.

The cannabinoids in the pharmaceutical composition described herein are present in a range of 2% to 15% by weight of the pharmaceutical composition.

In an embodiment, the cannabinoids may comprise of only CBD. In another embodiment, the cannabinoids may comprise of CBD in combination with other cannabinoids.

D-limonene, as known in the prior art, when applied topically is an algesic, however when combined in the topical pharmaceutical composition herein, rapid analgesic effects are obtained.

The component, ashwagandha extracts are derived from ashwagandha plants which is used as a medicinal herb for various diseases and as a dietary supplement. The ashwagandha extracts is a naturally occurring component, obtained from the ashwagandha plant.

The component, dimethyl sulfoxide (DMSO) is a chemical compound which is present in the form of a colorless liquid and is miscible in a wide range of organic solvents as well as water. DMSO is predominantly used as an analgesic, a vehicle for topical application of pharmaceuticals, as an anti-inflammatory, and an antioxidant.

The amount of DMSO present in the topical pharmaceutical composition is in a range of 0.01% to 2% by weight of the topical pharmaceutical composition. In an embodiment, the amount of DMSO is in a range of 1% to 2% by weight of the topical pharmaceutical composition.

The component, base is referred to as a substance which is mixed with one or more components to form a final product. The base is selected from a group consisting of a cream, gel or lotion.

In an embodiment, the base is a cream base. In another embodiment, the cream base comprises of vitamin E.

The pharmaceutical composition described herein, acts as a medicament for relieving muscle pain and joint pain. The topical pharmaceutical composition rapidly relieves the pain when applied to an affected area. The affected area herein is referred to an area wherein the sensation of pain is felt or the area from which the pain emerges.

The pharmaceutical composition which is in the form of a cream is applied topically to the affected area in order to relieve the pain from the affected area.

The pharmaceutical composition can be advantageously combined with other medicinal substances such as, opioids, anticonvulsants, without limiting the scope of the invention with relation to combinations known to those familiar in the art.

In an alternate embodiment, the base may be a gel, wherein said gel is applied to the affected area in order to relieve the pain from the affected area.

In another embodiment, the base may be a lotion, wherein said lotion is applied to the affected area in order to relieve the pain from the affected area.

The different therapeutic classes of medications that are useful to be used in addition to the combination of cannabinoid-containing plant extracts include but are not limited to: natural opium alkaloids, anti-epileptics, non-selective monoamine reuptake inhibitors, opioids, anilides, diphenylpropyl amine derivatives, acetic acid derivatives and related substances, platelet aggregation inhibitors excluding heparin, carboxamide derivatives, propionic acid derivatives, salicylic acid derivatives, local anaesthetics, non-steroidal anti-inflammatory or anti-rheumatic compounds, coxibs, topical non-steroidal anti-inflammatory compounds, opium alkaloids and derivatives, anaesthetics for topical use, drugs used in opioid dependence, hydantoin derivatives, oripavine derivatives, phenylpiperidine derivatives. To the topical pharmaceutical composition, anti-inflammatory and/or analgesic herbal extracts can be added. Anti inflammatory or analgesic medicinal mushroom or fungal extracts or antiinflammatory or analgesic terpenes such as monoterpenes, diterpenes or tripenes as are known in the art. A monoterpene is defined as a class of terpenes that has two isoprene units and have the molecular formula C10H16. Monoterpenes may be linear (acyclic) or contain rings (monocyclic and bicyclic). A terpene is defined as a compounds with a chemical formula of $(C_5H_8)_n$.

A method for the preparation of the topical pharmaceutical composition described herein, comprising d-limonene, cannabinoids, ashwagandha extracts and dimethyl sulfoxide (DMSO). The method comprises the steps of, forming a first mixture, forming a second mixture, mixing and storing the first mixture and the second mixture to obtain a third mixture and filtering the third mixture and adding a filtered third mixture to a base.

The step of forming a first mixture includes solubilizing CBD with an alcoholic-limonene based extract. The CBD is solubilized with the alcoholic-limonene based extract in a ratio of 1:1. The first mixture comprises CBD in a range of 50% to 80% by weight of the first mixture.

In an embodiment, the alcoholic-limonene based extract is ethanol-limonene based extract. The ethanol-limonene based extract includes 40% to 60% of ethanol by weight of the ethanol-limonene extract.

After solubilization, the CBD with the alcoholic-limonene based extract is refrigerated (at a temperature just above the freezing point of water and below or equal to 4 degrees Celsius) and in absence of light for a period of 3 days. The refrigerated CBD with the alcoholic-limonene based extract results in the formation of the first mixture.

The step of forming a second mixture includes mixing ashwaganda extracts and dimethyl sulfoxide (DMSO) in water, thereby forming the second mixture. The second mixture comprises DMSO in an amount of 10% by weight of the second mixture.

The first mixture and the second mixture are then mixed and stored in a desiccator for a predefined period and at a predefined temperature to obtain a third mixture. The predefined period for which the first mixture and the second mixture are stored is in a range of 48 hours to 72 hours. In an embodiment, the predefined period is of 48 hours.

The predefined temperature at which the first mixture and the second mixture are stored in the desiccator is approximately 95° F. The step of storing the first mixture and the second mixture results in the evaporation of the alcoholic content from the first mixture and the second mixture with the majority of d-limonene being preserved in the mixture.

After storing the first mixture and the second mixture for a predefined period and at predefined temperature results in obtaining a third mixture which is then filtered. The filtration step is performed to remove un-dissolved ashwagandha extracts from the third mixture and to obtain a filtered third mixture. The filtered third mixture comprises of dissolved ashwagandha extracts with d-limonene, cannabinoids and dimethyl sulfoxide (DMSO).

The filtered third mixture is then added to a base selected from a group consisting of cream, gel or lotion to obtain a pharmaceutical composition of the present invention, which may relieve muscle pain and joint pain thereby.

In one example a pharmaceutical composition in the form of a cream containing d-limonene, cannabinoid CBD and ashwagandha extracts with DMSO was tested. The cream was applied to post-surgical areas such as knees after arthroscopic surgeries, sprained ankles, shoulder injuries where acute joint pain and acute muscle pain is often experienced. It was observed that after applying the cream to the affected areas, the pain was reduced dramatically within less than 5 minutes and mobility/relief achieved was achieved within 5 minutes.

In the acute administration tests, the pharmaceutical composition in the form of a cream containing, d-limonene, CBD and the ashwagandha extracts was observed to be more efficacious for relieving the muscle pain and the joint pain when compared to a cream comprising of THC and CBD only. The cream containing the cannabidiol and the ashwagandha extracts as described in the example was exemplarily effective in relieving the joint pain and the muscle pain in a manner clearly superior to commercially available CBD creams or cream containing CBD and THC in combination. No risk of any central nervous system impairment was found.

The anti-inflammatory effects of the ashwagandha extracts with that of the d-limonene, cannabidiol and the DMSO provided a superior effect to that of CBD and or THC alone.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalence of the claims are to be embraced within their scope. Combinations of any of the methods, systems, and devices described herein-above are also contemplated and within the scope of the disclosed technology.

The invention claimed is:

1. A topical pharmaceutical composition, namely a cream or lotion, comprising:
   a base;
   terpene;
   cannabinoids in a range of 2% to 15% by weight of the pharmaceutical composition;
   ashwagandha extracts; and
   dimethyl sulfoxide (DMSO) in a range of 1% to 2% by weight of the pharmaceutical composition;
   wherein the terpene is d-limonene in a range of 1% to 10% by weight of the pharmaceutical composition.

2. The topical pharmaceutical composition of claim 1, wherein the pharmaceutical composition acts as a medicament for relieving muscle pain and joint pain.

3. A topical pharmaceutical composition, namely a cream or lotion, comprising:
   a base;
   terpene;
   cannabinoids in a range of 2% to 15% by weight of the pharmaceutical composition;
   ashwagandha extracts; and
   dimethyl sulfoxide (DMSO) in a range of 1% to 2% by weight of the pharmaceutical composition;
   wherein the cannaboids are CBD, and
   wherein the CBD is solubilized with an alcoholic-limonene based extract in a ratio of 1:1 and frozen in absence of light for a period of at least two days thereby forming a first mixture.

4. The topical pharmaceutical composition of claim 3, wherein the cannaboids consist only of CBD.

5. The topical pharmaceutical composition of claim 3, wherein the CBD is a synthetic CBD.

6. The topical pharmaceutical composition of claim 3, wherein the first mixture comprises CBD in a range of 50% to 80% by weight of the first mixture.

7. The topical pharmaceutical composition of claim 3, wherein the ashwagandha extracts and the dimethyl sulfoxide (DMSO) are mixed in water, thereby forming a second mixture.

8. The topical pharmaceutical composition of claim 3, wherein the alcoholic-limonene based extract is ethanol-limonene based extract.

9. The topical pharmaceutical composition of claim 8, wherein the ethanol-limonene based extract includes 40% to 60%, inclusive, of ethanol by weight of the ethanol-limonene extract.

10. The topical pharmaceutical composition of claim 7, wherein the second mixture comprises DMSO in an amount of 10% by weight of the second mixture.

11. The topical pharmaceutical composition of claim 7, wherein the first mixture and the second mixture are mixed and stored in a desiccator for a time period of 72 hours to 3 days and filtered and added to the base.

12. A topical pharmaceutical composition, comprising:
    a base;
    terpene;
    cannabinoids in a range of 2% to 15% by weight of the pharmaceutical composition;
    ashwagandha extracts; and dimethyl sulfoxide (DMSO) in a range of 1% to 2% by weight of the pharmaceutical composition;

wherein the base is selected as a cream and comprises vitamin-E.

* * * * *